United States Patent
Gaugler et al.

(10) Patent No.: US 6,432,698 B1
(45) Date of Patent: Aug. 13, 2002

(54) DISPOSABLE BIOREACTOR FOR CULTURING MICROORGANISMS AND CELLS

(75) Inventors: Randy Gaugler, North Brunswick, NJ (US); Moeen Abu Hatab, Knoxville, TN (US)

(73) Assignee: Rutgers, the State University, New Brunswick, NJ (US)

( * ) Notice: Subject to any disclaimer, the term of this patent is extended or adjusted under 35 U.S.C. 154(b) by 0 days.

(21) Appl. No.: 09/533,180

(22) Filed: Jan. 6, 2000

Related U.S. Application Data

(60) Provisional application No. 60/114,822, filed on Jan. 6, 1999.

(51) Int. Cl.$^7$ ................................................ C12M 1/09
(52) U.S. Cl. ........................... 435/296.1; 435/297.2; 435/304.1; 435/818
(58) Field of Search .................... 435/296.1, 297.2, 435/297.3, 304.1, 818

(56) References Cited

U.S. PATENT DOCUMENTS

| | | |
|---|---|---|
| 4,027,427 A | 6/1977 | Stoller et al. |
| 5,225,346 A | 7/1993 | Matsumiya et al. |
| 5,288,296 A | 2/1994 | McCabe et al. |
| 5,306,269 A | 4/1994 | Lewis et al. |
| 5,445,629 A | 8/1995 | Debrauwere et al. |
| 5,565,015 A | 10/1996 | Kobayashi |

FOREIGN PATENT DOCUMENTS

| | | | |
|---|---|---|---|
| EP | 0 343 885 | * 11/1989 | ............ C12M/1/04 |
| GB | 1380316 | 1/1975 | |
| GB | 2 202 549 | * 9/1988 | ............ C12M/1/00 |

OTHER PUBLICATIONS

Kaya, H.K. and Gaugler, R. Entomopathogenic Nematodes. *Ann. Rev. Entomol.* 1993. 38:181–206.

Lee, H.B., et al. *Handbook of Polymeric Biomaterials.* 1995. 581–597. CRC Press, Boca Raton.

Friedman, M.J. *Entomopathogenic Nematodes in Biological Control.* 1990. R. Gaugler and H.K. Kayu, ed., Boca Raton FL. CRC Press.

Georgis, R. *Entomopathogenic Nematodes in Biological Control.* 1990. R. Gaugler and H.K. Kayu, ed., Boca Raton FL. CRC Press.

* cited by examiner

*Primary Examiner*—David A. Redding
(74) *Attorney, Agent, or Firm*—Licata & Tyrrell P.C.

(57) ABSTRACT

A disposable bioreactor for culturing microorganisms and cells is provided. The bioreactor is suitable for use by individuals not skilled in microbiology or aseptic technique. It is constructed of flexible or semi-flexible waterproof sheets to form a container designed to provided mixing and gas exchange to microorganisms cultured therein. Mixing and gas exchanged are achieved by bubbling gas through the culture, either from a single locus at the lowermost apex of a container having a wedge-shaped or rounded bottom, or from multiple loci across a flat-bottomed container. Also provided is a kit for culturing a selected microorganism, preferably an entomopathogenic nematode or other organism useful as a biopesticide.

41 Claims, 6 Drawing Sheets

DISPOSABLE BIOREACTOR FOR CULTURING MICROORGANISMS AND CELLS

This application claims priority to U.S. Provisional Application No. 60/114,822, filed Jan. 6, 1999, the entirety of which is incorporated by reference.

FIELD OF THE INVENTION

This invention relates to the field of microbial fermentation and biopesticide production. In particular, this invention provides a disposable bioreactor for use in culturing microorganisms and other cells.

BACKGROUND OF THE INVENTION

Various scientific articles are referred to throughout the specification. These articles are incorporated by reference herein to describe the state of the art to which this invention pertains.

Current agricultural practices make use of pesticide strategies that are predominantly based on chemicals. Public concern about the environmental hazards of chemical pesticides has increased in recent years. While the range of environmentally safe biological control agents has been growing, growers still rely on the chemical alternatives. Biological control agents offer many advantages over conventional chemical pesticides, but they have been slow to gain acceptance because they are more difficult to produce, distribute and apply.

One biological control agent with great potential is the entomopathogenic nematode. While some species of nematode are phytopathogenic, others are not. Among the non-phytopathogenic species are those which are entomopathogenic and proven useful in controlling pathogenic insects on crop plants. These nematodes, from the families Steinernematidae and Heterorhabditidae, are mutualistically associated with bacteria from the genus Xenorhabdus. Together they have an extraordinarily high host range that spans nearly all the insect orders. This wide host range is a major reason why these families of nematodes have great agricultural and economic value (Kaya and Gaugler, 1993, Ann. Rev. Entomol. 38:181–206).

In spite of these advantages, the use of 10 nematodes as a biological control agent has been slow to develop. Key problems have been the development of up-scalable culturing techniques, stable storage conditions, transporting the product without loss, and reliable application formulations. Production costs per hectare of nematode cultures exceed those of most chemicals. The relatively short shelf-life of nematodes of a few weeks as well as their restricted temperature range necessitates special handling and contributes to inconsistent performance. Formulations designed to improve the stability and performance of the product are expensive. Strains of nematodes that are efficacious when freshly produced and applied in a research scale frequently do not perform well on an industrial scale. These problems restrict the use of nematodes to primarily high-value specialty crops, and even for these crops, the expense and expertise needed to successfully culture nematodes for biocontrol is beyond the scope of the typical grower or local producer of biopesticides.

The development of disposable micro-culture technology would permit local production of nematodes and other biological control agents, and would alleviate many of these problems. Local production eliminates both the hazards of distribution and storage. Fresh cultures would also be in their most efficacious form for applications. Finally, inexpensive small-scale production of the biological control agents eliminates the most costly elements the existing commercial production scheme: formulation, storage, transport, waste disposal and starting capital.

Conventional microbial fermentation systems generally are composed of a rigid container (e.g., stainless steel or glass) having a means for aerating and mixing the culture contents (e.g., an air inlet port and an impeller or some other mixing means). Clearly, such equipment is not intended to be disposable, and therefore is not suitable for on-site use in small scale production of microorganisms. For local microculture to be a success, a disposable micro-culture container must be developed. Such a container should be inexpensive, disposable and easy to use. It should be made of a material that is sterilizable, strong enough to allow the scale-up of culture size, and manufacturable by existing technology. Finally, the design should be one that is flexible and will allow the culturing of a wide range of cells under both aerobic and anaerobic conditions.

Previous attempts have been made to develop disposable culture containers for microbial fermentation. For instance U.S. Pat. No. 5,565,015 discloses a disposable fermenter comprising a flat-bottom plastic container with a flexible flat tube for introduction of liquid. G.B. Patent No. 1,380,316 discloses a flat-bottom plastic container having a somewhat elongated, narrow neck terminating in a releasably closeable mouth that serves as a port for addition of liquid and for communication with the outside atmosphere. Though these disposable containers may be suitable for culturing certain microorganisms under specific conditions, they are not suitable for culturing a wide range of microorganisms, particularly those requiring good aeration or gas exchange, and long culture times.

SUMMARY OF THE INVENTION

The present invention provides an apparatus and system for culturing cells or microbial organisms that is disposable, easy to use, inexpensive and versatile. The invention enables the preparation of microorganisms by people not specifically trained in microbiology or aseptic technique. It enables microorganisms to be grown safely, for a variety of purposes, without the need for specialized facilities such as temperature controlled rooms, laminar flow cabinets and sterilization equipment.

According to one aspect of the invention, a disposable bioreactor for culturing microorganisms or cells is provided. The bioreactor comprises flexible or semi-flexible waterproof sheets, preferably plastic, sealed along their edges to form a container. In one embodiment, the container has a wedge shaped or rounded bottom to facilitate mixing and aeration by eliminating "dead space" in corners, and features a means located at the lowermost extremity of the rounded or wedge shaped bottom for generating gas bubbles for mixing and providing gases to microbial or cellular liquid cultures within the container. In another embodiment, the container has a flat bottom and features a series of gas bubble generators situated at intervals along the bottom. In each of these embodiments, the gas bubbler or series of bubblers is situated such that gas bubbles are generated at the bottom of the container and rise to the top. During their transit from the bottom to top of the container, the bubbles tend to get smaller, which facilitates gas exchange. In preferred embodiments of the invention, a gas diffuser is operably attached to the bubbler, to break larger bubbles into smaller bubbles.

The container comprises at least one inlet port for introducing gases or liquids and at least one exit port for exhausting gases or removing liquids. The gas inlet port is attached to a gas pump by tubing, which preferably contains one or more filters for removing microbial contaminants from the gas stream. The outlet port further comprises an exhaust tube extending therefrom, between about 3 inches and about 5 feet in length. In a preferred embodiment, the exhaust tube is coiled to serve as a condenser for liquids evaporating during the culturing process. The exhaust tube may further comprise a valve to prevent back flushing of liquids to the interior of the container, and a filter for filtering microbial contaminants.

The disposable bioreactor of the invention also may contain an inoculation port for introducing inoculant into the container. It may further comprise a breakable pouch on an interior face of the container, or a separate external chamber connected by tubing to the bioreactor chamber, for delivery of concentrated or dried growth medium, inoculum, or other substances. Other features are described in detail below.

According to another aspect of the invention, a kit is provided for culturing a microorganism, which comprises: (a) a disposable bioreactor as described above; and (b) instructions for using the disposable bioreactor to culture the microorganism. In various embodiments, the kit further comprises one or more of the following: (c) ingredients for preparing, or prepared culture medium for culturing the microorganism; (d) inoculum of the microorganism to be cultured; (e) accessories for attaching the bioreactor container to a local source of water for filling the container; (f) accessories for connecting the bioreactor inlet port to a gas pump; and (g) a gas pump.

In preferred embodiments, the kit is specifically adapted for culturing a microorganism selected from the group consisting of bacteria, cyanobacteria, fungi, algae, protozoans and nematodes. Most preferably, the kit is adapted for culturing entomopathogenic nematodes for use as biopesticides.

Other features and advantages of the present invention will be better understood by reference to the drawings and detailed description that follow.

BRIEF DESCRIPTION OF THE DRAWINGS

FIG. 5. Views of a culture container with a flat bottom and a series of inlet holes for generating gas bubbles.

DETAILED DESCRIPTION OF THE INVENTION

Figure 1A:
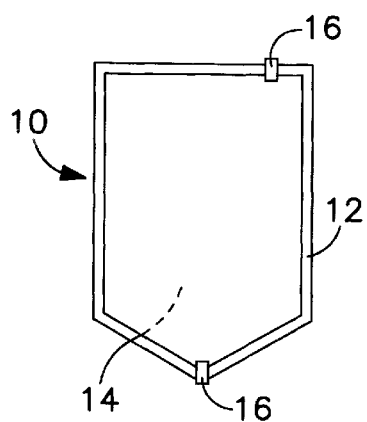
FIG. 1. Schematic diagram of several basic culture container designs.
Figure 1B:
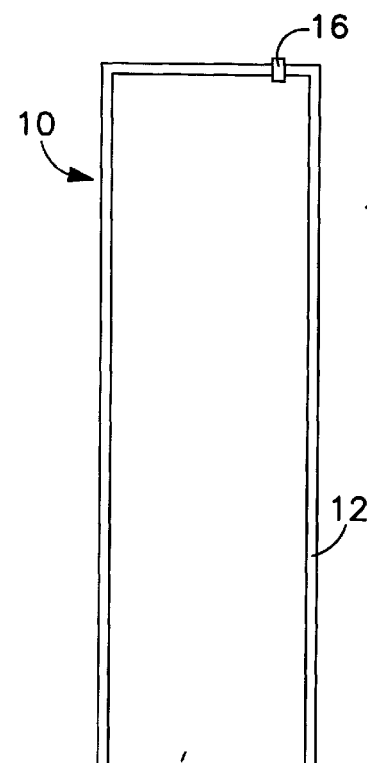
Figure 1C:
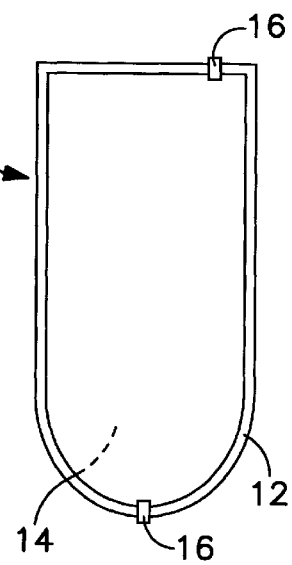

The present invention provides disposable devices for culturing a wide variety of microorganisms, both aerobic and anaerobic. These devices are designed for use by persons not specifically trained in microbiology or aseptic technique. They are particularly suitable for local microfermentation of organisms for biological control in an agricultural system. They can also be used for fermentation of wine or beer. The organisms that may be successfully cultured in the disposable culture containers of the present invention include, but are not limited to, bacteria, cyanobacteria, fungi, certain algae, protozoans and nematodes. As described in greater detail below, these culture containers are particularly suited for culturing entomopathogenic nematodes for use in biological control of insect pests. The bioreactor may also be used to culture other kinds of entomopathogenic and plant pathogen antagonistic biocontrol agents.

Referring now to the drawings, FIG. 1 shows several container shape designs for the disposable bioreactor of the present invention. The container (10) is constructed of flexible or semi-flexible, waterproof sheets, which are sealed along their edges (12) to create an interior (14). As illustrated, the container is fashioned with one or more ports (16) for introduction or removal of gases or liquids. FIG. 1A shows a generally flat container (10) with a wedge-shaped bottom, at the apex of which is an inlet port (16). An exit port (16) is positioned in the upper right hand corner of the container (10). FIG. 1B shows a similar container (10), but elongated as compared to the design shown in FIG. 1A. This style can be used if greater gas exchange is desired, inasmuch as gas bubbles originating at the bottom of the container continue to decrease in size as they travel the extended distance to the top of the container. FIG. 1C shows a container (10) with a rounded bottom. FIG. 1D shows a container (10) with internal partition (18) that creates a draft tube (20). The bottom of the container tapers into an asymmetric wedge, where an inlet port (16) is located. Gas bubbles introduced into the interior (14) through the port (16) are forced into a directional flow around the partition, as shown by the arrows. FIG. 1E shows a four-sided container (10) with wedge-shaped bottom having an inlet port (14) at the apex. FIG. 1F shows a container (10) with a flat bottom and an inlet port (16) in the upper right hand corner, in communication with a gas reservoir (32) that directs incoming gas to the floor of the container, where it enters the container at multiple locations via small inlet holes (34). In this design, the entire floor of the container receives gas bubbles, so settling of the organism does not occur.

Figure 2:
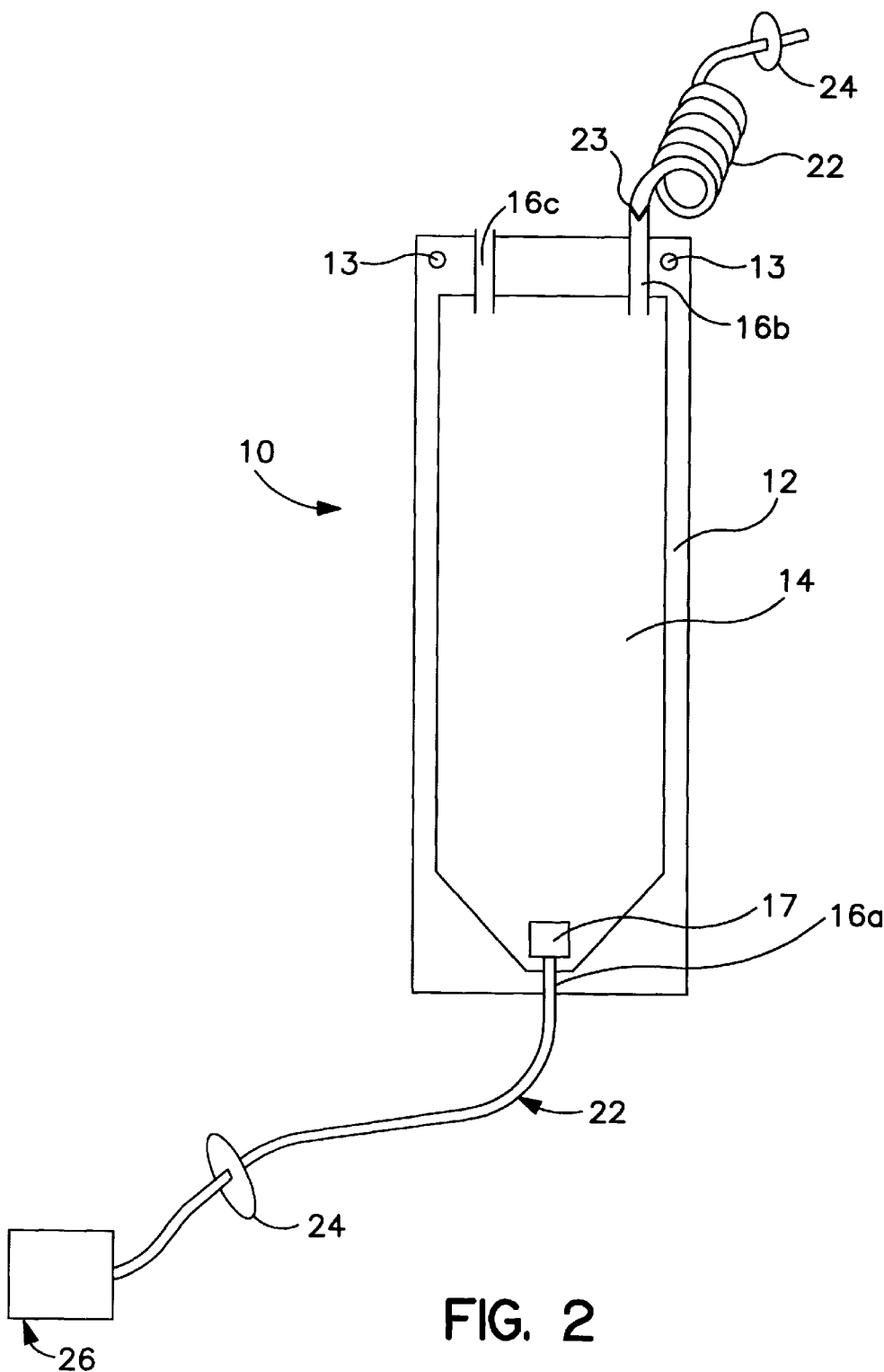
FIG. 2. Perspective view of a culture container with three ports, including air inlet port connected to micro-filter and air pump, exhaust port connected to coiled tube and micro-filter, and injection port.

FIG. 2 shows one preferred embodiment of the invention. This bioreactor comprises a container (10) of flexible, waterproof sheets, sealed along their edges (12) to create an interior (14). The upper edge (12) is constructed with holes (13) for hanging the container (10) As illustrated, the container is fashioned with an inlet port (16a), an outlet port (16b) and an inoculation port (16c). The inlet port (16a) is shown as a gas inlet, which further comprises a gas diffuser (17) operably attached to the port on the interior side. The inlet port is connected to a gas pump (26) by tubing (22). A micro-filter (24) is placed in the tubing (22) between the gas pump (26) and the inlet port (16a). The container (10) further comprises an exit port (16b), which functions as an exhaust vent. The exit port (16b) as illustrated further comprises a length of tubing (22), coiled to serve as a condenser for liquid evaporating from the culture medium during the culture period. The coiled tubing (22) contains one or more valves (23) to prevent back flushing of culture medium or condensate. The exit port tubing (22) is also fitted with a micro-filter (24) to prevent contamination.

Figure 3:
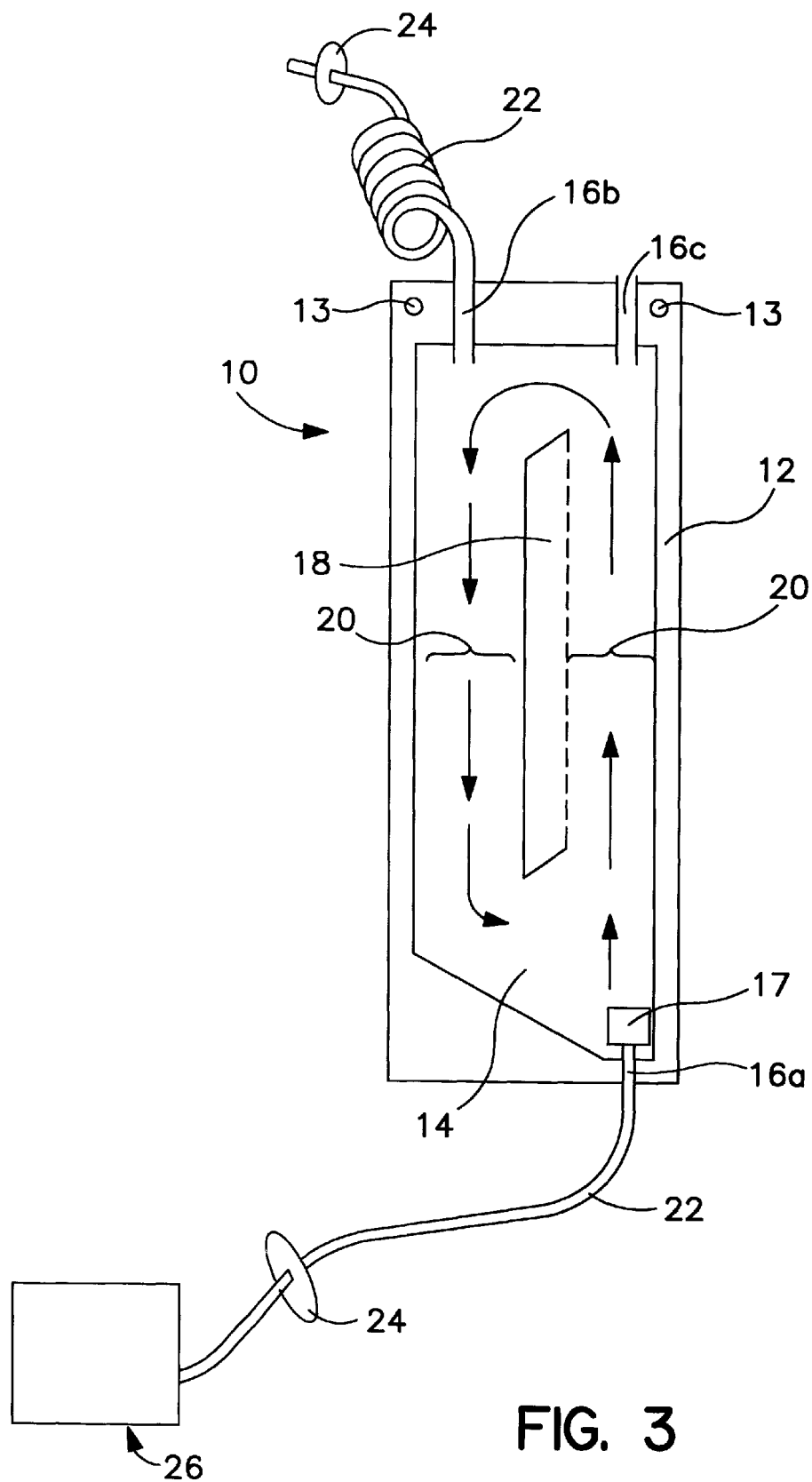
FIG. 3. Perspective view of a culture container with three ports, further comprising an internal baffle, partially dividing the internal compartment to form a draft tube. Introduction of gas through the gas inlet port causes flow of culture contents around the draft tube, as shown by the arrows.

FIG. 3 shows another preferred embodiment of the invention. In this embodiment, the container (10) comprises an asymmetrically wedge shaped bottom, and further comprises a partition (18) that partially divides the interior (14) longitudinally. The partition (18) is constructed so that liquid can move either over or under the partition (18). The partition (18) as illustrated is constructed by welding the front and back of the container together to produce the specified length of partition. Division of the interior (14) by the partition (18) creates draft tubes (20) inside the container. The inlet port (16a) is a gas inlet as described in FIG. 2, operably attached to a gas diffuser (17). Introduction of gas bubbles into the container via the gas inlet causes liquid inside the container to flow around the partition (18), through the draft tube (20), in the direction shown by the arrows.

Figure 4:
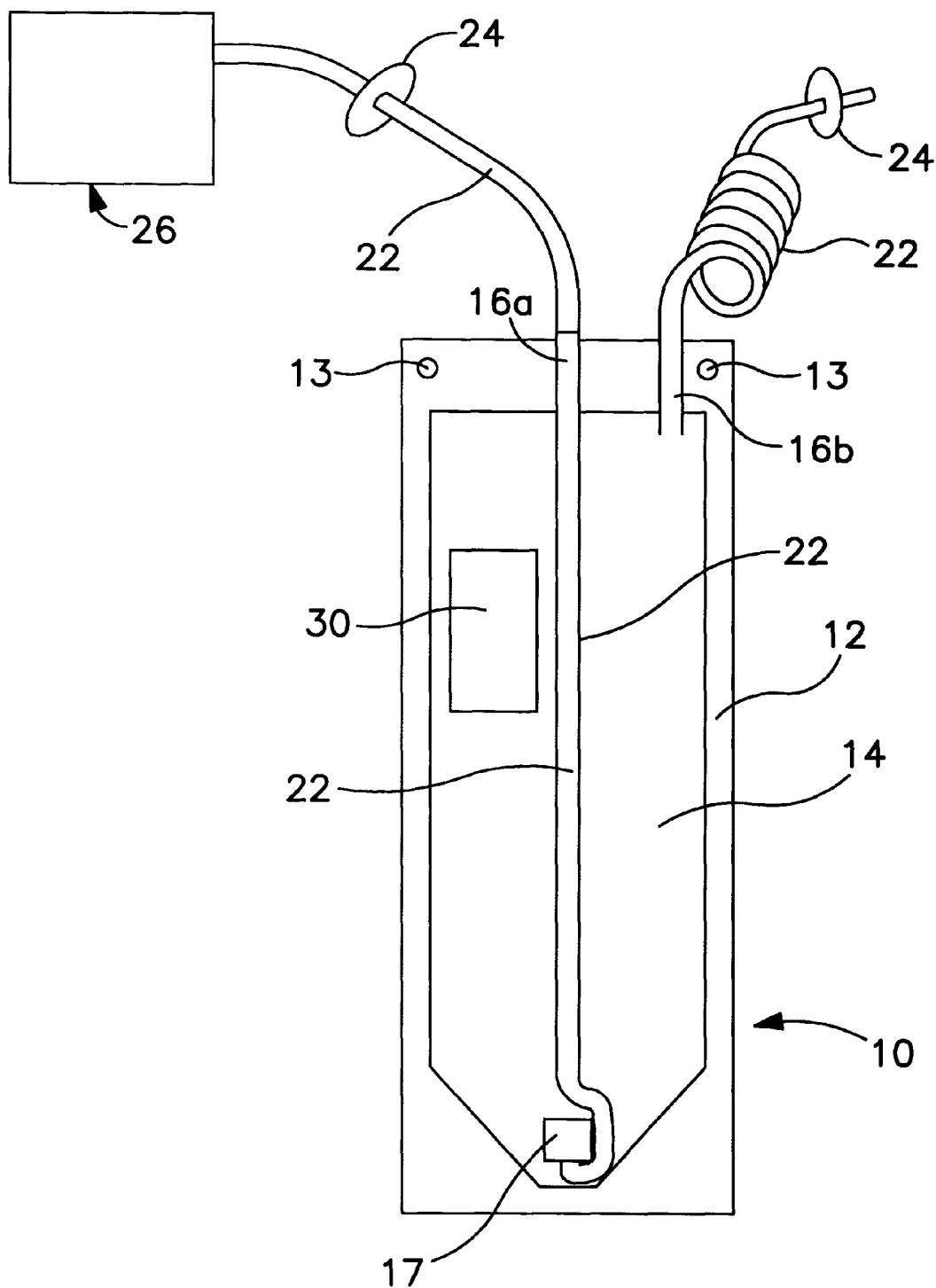
FIG. 4. Perspective view of a culture container with two ports and a breakable internal pouch for pre-loading with dehydrated culture medium or inoculum.

FIG. 4 shows another preferred embodiment of the invention. As illustrated, the inlet port (16a) in the container (10) is a gas inlet, attached by tubing (22) to a gas pump (26), the tubing (22) further containing a micro-filter (24). However, in this embodiment, the gas inlet port (16a) is positioned at the top of the container (10), and a length of tubing (22) internal to the container directs gas bubbles to the apex of the wedge-shaped bottom of the container, where the tubing is operably attached to a gas diffuser. This variation allows port positioning to be independent of the functioning of the container, so that port position can be chosen to suit support system, pump position, manufacturing and/or structural constraints. Also in this embodiment, the container (10) contains an outlet port (16b) but no inoculation port (16c). Instead, the container (10) is constructed with an internal, breakable pouch (30) which may contain nutrient concentrate, or inoculum, or both.

Figure 5A:
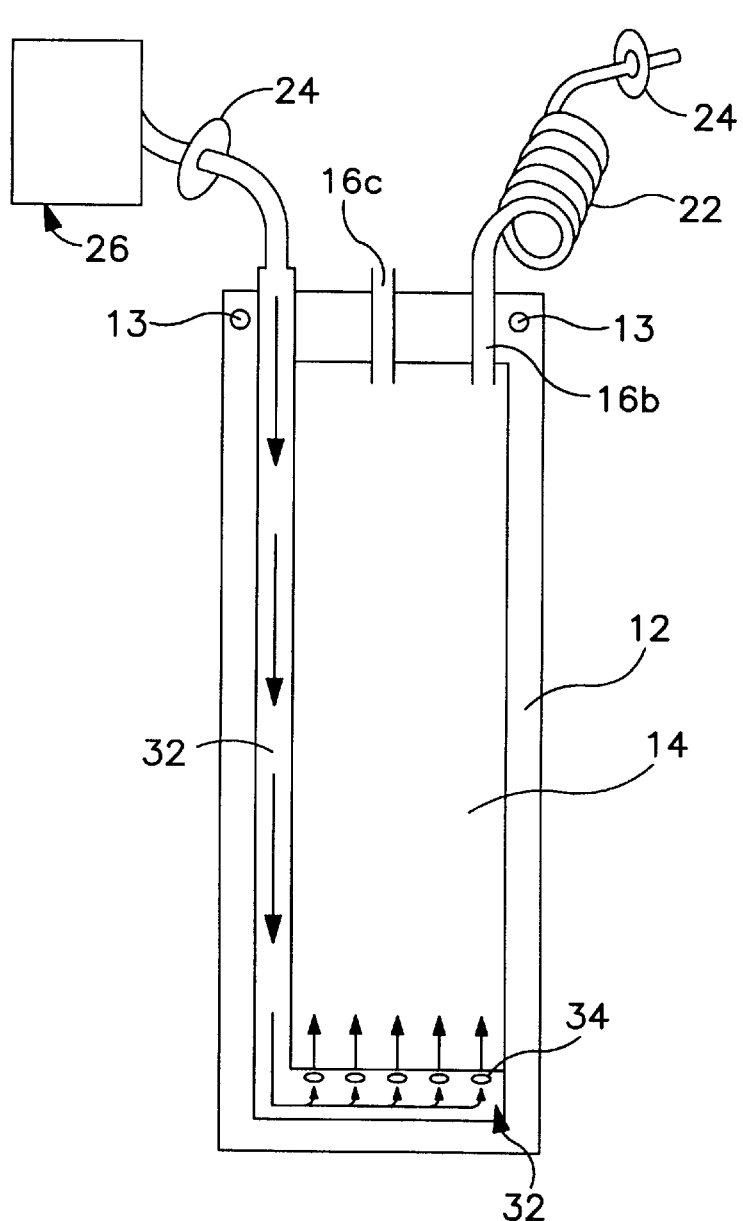
FIG. 5A shows a perspective view of one culture container having a gas inlet reservoir with multiple inlet holes built into the container.
Figure 5B:
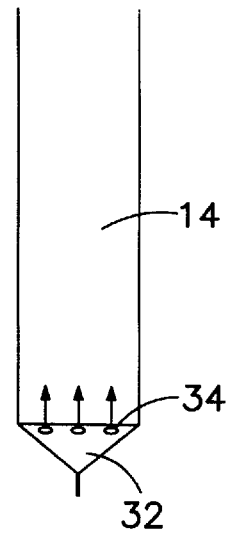
FIG. 5B and FIG. 5C show cross-sectional views of two different types of containers with built-in gas inlet reservoirs.
Figure 5C:
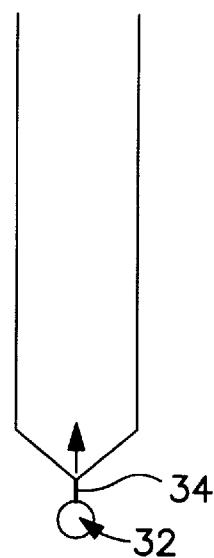

FIG. 5 shows another preferred embodiment of the invention. As illustrated in FIG. 5A, the inlet port (16a) is a gas inlet leading to a gas reservoir (32) built into the container. The gas reservoir is fashioned with multiple small inlet holes (34) to permit gas from the reservoir to bubble into the interior (14) all across the floor of the container (10). FIG. 5B shows one design for the gas reservoir (32), wherein it is partitioned from the interior (14) by a partition (36) having numerous inlet holes (34). FIG. 5C shows another design for the gas reservoir (32), wherein it is connected to the container (10) by a weld, perforated with inlet holes (34) to enable passage of the gas from the gas reservoir (32) to the interior (14) of the container.

Figure 6:
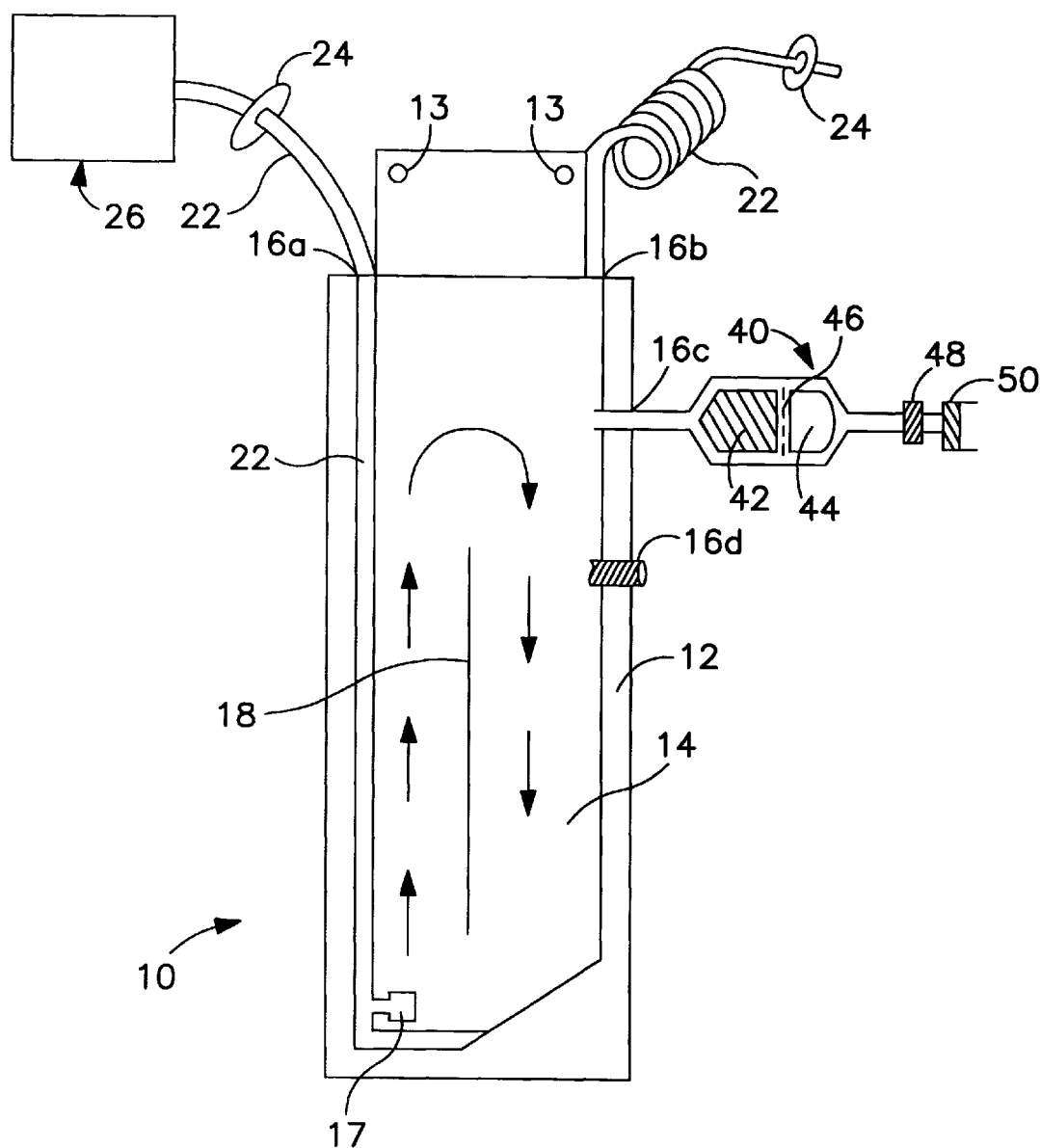
FIG. 6. Perspective view of a culture container with four ports and an external reservoir for pre-loading with dehydrated culture medium or inoculum.

FIG. 6 shows another preferred embodiment of the invention. Like the embodiment shown in FIG. 3, the container (10) in this embodiment comprises an asymmetrically wedge shaped bottom, and further comprises a partition (18) that partially divides the interior (14) longitudinally. The partition (18) is constructed as described in FIG. 3, resulting in creation of draft tubes (20) inside the container, as depicted by the flow of the arrows. In this embodiment, as in the embodiment illustrated by FIG. 4, the gas inlet port (16a) is positioned at the top of the container (10), and a length of tubing (22) internal to the container directs gas bubbles just to the lowermost portion of the asymmetric wedge-shaped bottom of the container, where the tubing is operably attached to a gas diffuser (17). In this embodiment, the container further comprises an external reservoir (40), with a chamber (42) for dried or concentrated growth medium and a chamber (44) for inoculum, separated by a breakable septum (46). The external reservoir is connected by tubing on one end to the interior of the container by a port (16c), and on the other end to a tap water supply (50). The tap water flows through a water purification filter (48) into and through the external reservoir, forcing the contents thereof into the interior of the container. A fourth port (16c) is included as a sampling port.

At minimum, the disposable bioreactor of the present invention has three parts: the container itself, an inlet port and an outlet port. The inlet port can serve as an air inlet and a drainage tube after the unit has been used. The outlet port can serve as an air outlet and a water/medium fill tube. Alternatively, additional inlets or outlets may be fashioned in the container.

Two principles of microbial fermentation are important to understand in order to appreciate design features of the disposable unit of the invention. These are (1) suspension of the microorganism in the growth medium, and (2) proper aeration of the medium to support growth of the microorganism. Proper suspension of microorganisms in the growth medium helps with aeration, i.e., good contact of the microorganism with dissolved gases in the medium. Good suspension also is important for good access to the nutrients and other growth factors in the culture medium. Proper aeration involves ensuring that there are sufficient dissolved gases in the medium to support growth of the microorganism. The term "aeration" is used in the present specification with reference to aerobic organisms, will most commonly be cultured in the disposable micro-fermenters of the present invention. However, persons skilled in the art will appreciate that proper gas exchange for anaerobic organisms is also important, and the term "aeration" as used herein is considered to encompass gas exchange of any type.

In a standard fermenter (e.g., a stainless steel fermenter), two means are used to achieve proper aeration and proper circulation of the microbes (1) bubbling air (or other gas) through the growth medium in the fermentation chamber and (2) an impeller (stirrer) to effect a mechanical circulation. Using the disposable bioreactor of the present invention, aeration and suspension are accomplished without the use of an impeller. Thus, the gas bubbles must function for both purposes.

Generally, gas bubbles are introduced into the bioreactor at the bottom, and they naturally rise to the top. As they rise, they tend to get smaller. As they get smaller, they are more available to deliver gases to the microbes. However, the larger bubbles tend to be more effective at moving the liquid around and maintaining the microbes in suspension. The bioreactor container of the present invention is designed to promote maximum aeration and suspension of microbes without the use of an impeller. As such, it is important that the "dead space" in the bag is minimized. Dead space is found in corners, where it would be difficult to effect circulation with bubbles alone. Accordingly, in one preferred embodiment, the container is designed so as not to have square corners at the bottom. The bottom is generally wedge-shaped, with the air inlet at the apex of the wedge. Alternatively, the container may be rounded at the bottom. In another embodiment, the container is designed with square corners at the bottom, but in this case further comprises multiple points for generating gas bubbles, situated along the entire floor of the unit. This embodiment is expected to be most useful for smaller containers, e.g., 20 L or less. FIG. 1 shows several representative container designs.

Figure 1D:
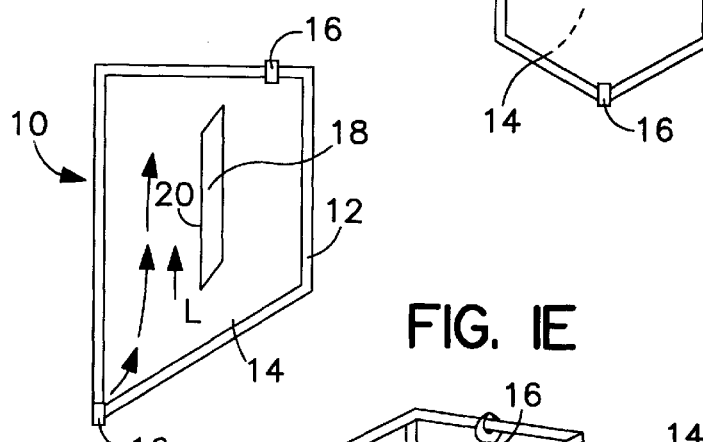
Figure 1E:
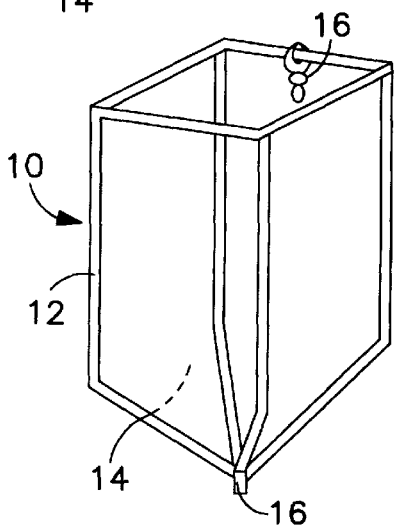
Figure 1F:
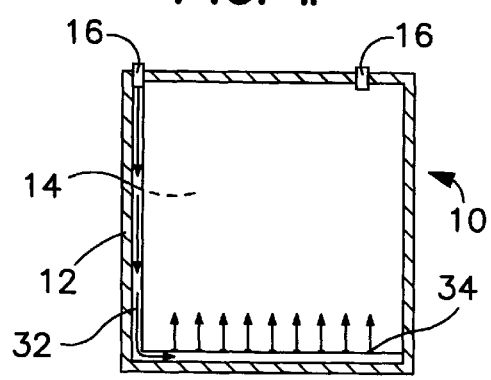

The dimensions and shape of the cell culture container can be varied to suit the needs of expense, manufacturer and specific cultures. Along with gas exchange and mixing, other key criteria to selecting a container shape include shear force and cell yield. A two-dimensional container that is longer than wider is preferred, and the desired length to width ratio is 3.0. A wide range of interior volumes is contemplated, ranging from 1 L to 200 L or more. Preferably, the containers are 5–100 L in interior volume. Although a rectangular shape is illustrated in the figures, other shapes can also be used to advantage. These shapes include, but are not limited to, an inverted triangles and elongated diamond shapes. Three-dimensional containers are also contemplated for use in the present invention, as illustrated in FIG. 1E. Sheets of plastic may be used to form three-dimensional containers by making more than two walls, or incorporating pleats or darts in a two-walled structure. The container may also be made of molded plastic, using similar technology used to make milk cartons.

The container is constructed from flexible or semi-flexible, waterproof material, preferably plastic. Polyvinyl chloride sheets (or other inert plastic) have been used in the instant invention, but other kinds of plastic are suitable, and may also be desirable in special circumstances. Plastic may be chosen for light transmitting qualities. Certain cells may be sensitive to bright white light or ultraviolet radiation, and for these cells the container can be made of plastics the absorb these wavelengths. Likewise, other kinds of cells, plant cells for example, may be developmentally regulated by the spectral quality of light, and for these cells the culture container can be made of plastics that selectively transmit the desired wavelengths of light.

The strength of the plastic is also an important consideration. For example, for smaller containers, 14-gauge PVC sheets are suitable; however for larger culture containers, stronger plastics may be desirable. On way to increase the strength is to increase the thickness and/or the formulation of the plastic. Alternately, strengthening fibers can also be added to the PVC sheets. Finally, different kinds of plastic can be used, according to standard practice.

Other characteristics of the material used for making the container may be important in culturing various types of cells or microorganisms. The inside of the container may be treated with substances that increase or decrease cell adhesion, depending on the culture conditions desired and the kind of cells.

In a preferred embodiment, the container is constructed with welded seams, in accordance with techniques that are well-known in the art, e.g., for production of plastic medical bags (blood bags) and the like. Other means to seal the seams of the container are also known in the art, and include, but are not limited to, heat, ultrasound and radiowave welding. Other kinds of plastic may lend themselves to other kinds of manufacture, such as mold injection.

The container comprises one or more ports to serve as inlets or outlets for gases or liquids. The ports are constructed of rigid or semi-rigid materials that are compatible with the material used for construction of the container. In preferred embodiments, any standard plastic tubing or molded plastic can be used to construct the ports, and they are welded into the seams of the container according to standard techniques. A variety of such ports are commercially available, e.g., for use in medical bags and similar containers. The structures that form the ports can also be varied, e.g., to accommodate different volumes of media, autoclave techniques and port functions. These ports may have any of the port variations known in the art, including but not limited to, Luer-lock fittings, rubber sheet gaskets and frangible valves.

The disposable bioreactors of the present invention preferably are pre-sterilized prior to shipping to the local user. Various sterilization techniques may be used. The choice of technique is partially dependent on the type of plastic chosen (Lee et al., 1995, in *Handbook of Polymeric Biomaterials*, CRC Press, Boca Raton, p 581–597). Sterilization techniques that are common in the art include, but are not limited to, dry heat, autoclaving, radiation, and ethylene oxide gas.

The disposable bioreactor may be pre-packaged with concentrated or dried medium and microbial inoculum. Dried medium can be included as a cake in a pre-sterilized bioreactor. FIG. 4 shows one embodiment wherein dried or concentrated medium or microbial inoculum is pre-packaged in the unit in an internal, breakable pouch. FIG. 6 shows another embodiment wherein dried or concentrated medium or inoculum is pre-packaged in an external reservoir, connected by tubing through a port to the interior of the container. Alternatively, the user may wish to add the inoculum separately from the medium. In this case the bioreactor is fitted with an inoculation port, for injecting or otherwise introducing the inoculum into the container.

The bioreactor of the instant invention may be supported by several means. The container may be hung by holes in the top of the container outside the seam, or by hooks attached to the top of the container. Alternately, the flexible plastic container may be placed in a rigid outer container. Finally, the container can be constructed of a semi-flexible plastic that can support itself.

The bioreactor can be equipped with optional devices to aid in the culture of cells and microorganisms. These devices include, but are not limited to, thermometers, gas evaluation systems (i.e. $CO_2$ or $O_2$), means to evaluate cell density and volume calibration markings.

Air or other gas is introduced into the container via a gas inlet port. Tubing connecting the port to a gas pump is fitted with at least one filter, for filtering microbes from the airstream prior to introduction of the gas into the bioreactor. The tube preferably is adapted for use with a commercially available air pump, such as an aquarium air pump.

In one embodiment, illustrated in FIGS. 1–3, the gas inlet port is positioned at the bottom apex of the bioreactor container. It may or may not be fitted with a gas diffuser. In another embodiment, illustrated in FIGS. 4 and 6, the gas inlet port is positioned at the top of the container, but it is fitted with internal tubing that reaches down to the bottom apex of the container, where it is affixed to the container. In yet another embodiment, illustrated in FIG. 5, the gas inlet port is positioned at the top of the container, and communicates with an internal gas reservoir or tube that runs down the side of the container and across the bottom. In this embodiment, air bubbles are introduced all along the floor of the container via small inlet holes between the gas reservoir and the interior of the container. In a modification that incorporates some of the features illustrated in FIGS. 4 and 5, the "gas reservoir" may simply comprise an internal tube running down the side of the container and affixed across the bottom, and having perforations in the portion that runs across the bottom of the container.

In preferred embodiments, the gas inlet port is fitted with a gas diffuser. This is sometimes called a "sparger". The function of the diffuser is to break large gas bubbles into smaller bubbles, and further to accelerate them into the medium. Again, spargers are commonly used in aquaria. Any device that accomplishes the task of breaking gas bubbles can be used in the present invention. Preferably they are inexpensive enough to be disposable, along with the bioreactor.

Another way to facilitate circulation (thus aeration) of the microorganisms in the bioreactor is to construct the bag to have a draft tube. A draft tube is created by placing a divider or partition within the chamber that acts to direct the flow of circulation in a certain way. In a simple two-dimensional bag, as illustrated in FIG. 1D, FIG. 3 and FIG. 6, the draft tube is constructed by fusing the plastic sides together for a specified length, parallel to the direction of flow of the gas. The gas then forces medium and microbes up one side of the partition, over the top, and down the other side, creating a circular flow in the bioreactor. The draft tube can also be made in a two- or three-dimensional container by putting a partition in the bag, which allows for flow over the top of the partition and around under the bottom of the partition.

The bioreactor comprises a vent to exhaust gas. The vent in the bioreactor of the present invention preferably comprises an outlet port fitted with tubing, of varying length and with certain features. The tube serves two main functions: (1) it acts as a condenser to minimize evaporation of the medium during the fermentation; and (2) it acts as an obstacle to the ingress of airborne contaminants into the bioreactor. The longer the time needed to conduct a particular fermentation, the longer should be the outlet tube. Thus, short fermentations of a few hours could use a reactor with an outlet tube only inches long (2–6). Long fermentations, e.g. of nematodes, which can take 2 weeks, will need a tube 2–5 feet long. Preferably, longer tubes are coiled.

The outlet tube can be fashioned to also prevent back flushing of the growth medium, e.g., which could occur if the bag is squeezed and media is forced up into the tube. This is prevented by fitting the outlet tube with a valve that prevents back flushing of medium into the container.

As mentioned above, the outlet port can also be an inlet port for filling the bioreactor with growth medium or water. In this case, it is designed with tubing adaptable for hooking up to a standard water supply, such as a faucet or garden hose. It is further fitted with filters for removing contaminating microorganisms from the medium or water. In a preferred embodiment, the disposable bioreactor is packaged with a fitting that can connect with a filling tube for filling the bag, and with a different air outlet tube. The filling tube will have the aforementioned filters and adaptations for standard water supply. The air outlet may be fitted with a filter to prevent contamination from the ambient air and with a valve to prevent back flushing.

For convenience and ease of use, the disposable bioreactor of the present invention is packaged and sold as a kit. Typically, a kit can contain one or more disposable bioreactors (e.g., 5 L–200 L in size), with dehydrated media, inoculum, fittings, optional air pump (re-useable) and instructions for using the apparatus. The user supplies water, electricity and space to hang or otherwise support the bioreactor. The kit described below is designed particularly for use in growing nematodes.

The bioreactor, medium and inoculum are provided pre-sterilized in the nematode growing kit. The user fills the container with tapwater, via faucet or garden hose using the existing outlet port or a separate fill port, thereby hydrating the medium. The incoming water is sterilized via one or more in-line filters (e.g., 5 $\mu$M pre-filter obtained from a household water filtration unit, combined with a microbiological final filter (0.45 $\mu$M). The exhaust port is fitted with an extended exhaust tube, e.g., 2–5 feet in length, coiled, terminated by a 0.45 $\mu$M micro-filter. The air pump is connected to the gas inlet port with tubing containing an in-line micro-filter to sterilize the air. It should be noted that the size of the air pump varies with the size of bioreactor; however, a single large pump can run several units if a suitable gang-valve is included in the kit. The gas inlet port is operably attached internally to a gas diffuser, preferably a simple aquarium sparger.

For the nematode culture kit, dry medium components are incorporated as a "cake" into the bioreactor container and hydrated when the unit is filled with water. Liquid components may also be used if the bioreactor container is fitted with a breakable internal pouch.

A typical nematode culture medium comprises the following ingredients:

| | |
|---|---|
| Yeast extract | 10 g/L |
| Casein | 10 g/L |
| Milk Powder | 35 g/L |
| Salts: | |
| NaCl | 4 g/L |
| KCl | 0.3 g/L |
| CaCl$_2$ | 0.3 g/L |
| Lard | 28 g/L |
| Lecithin | 2 g/L |

Other suitable media include, but are not limited to, those referenced in Friedman (1990, in *Entomopathogenic Nematodes in Biological Control*, R. Gaugler and H. K. Kaya, ed., Boca Raton Fla., CRC Press).

The inoculum can be added via a separate inoculation port, which preferably contains a rubber septum to facilitate the introduction of low-stability inoculum, such as nematodes. Nematode inoculum alternatively may be placed in gelatin capsules and stored within the bioreactor, but only if the unit is shipped under low temperature, then used immediately. Nematodes may be stored in other forms, including but not limited to, hydrated forms kept moist on sponges or in vermiculite, alginate and polyacrylamide gels, or partially desiccated. These methods are described and referenced in Georgis (1990, in *Entomopathogenic Nematodes in Biological Control*, supra). The storage forms that are hydrated are unstable and need to be refrigerated and used promptly. The desiccated or partially desiccated forms are more stable and more tolerant to temperature changes.

Once the bioreactor is filled with medium, inoculated and hooked to the air pump, the microorganisms are cultured for a pre-determined amount of time, under specified culture conditions, according to the instructions provided with the kit. When the culture is complete the contents are harvested, e.g., by draining the container through one of its ports. When used for producing biological pesticides, the bioreactor contents simply may be poured into a spray tank.

The aforementioned bioreactor kit has been exemplified for the cultivation of nematodes. However modest adjustments can adapt the kit for use with many other cells and organisms. The kit may be adapted to culture other kinds of entomopathogenic and plant pathogen antagonistic biological control agents, including but not limited to, Beauveria, Metarrhizium, Steinemena, Serratia, Xanthomonas and Bacillus. Adjustments include different media and inoculum formulations and different sized cell culture containers, all of which would be known to one skilled in the art. For instance, bacterial inoculum may be lyophilized and transferred into a gelatin capsule that is stored within the bioreactor. Spore-forming bacteria or fungi would not require such encapsulation.

The culture container kit also has utility in growing a wide variety of cells including, but not limited to, plant cells, bacteria, yeast, mammalian cells and insect cells. It will be appreciated by one skilled in the art that the composition of the medium, antibiotic, and inoculum can be selected to aerobically culture a wide variety of cells and organisms. The temperature of growth, flow of air and duration of culture can also be adjusted to suit specific cells. Other adjustments may include aeration with different gases, e.g., $CO_2$ in the case of plant cells or $H_2S$ for sulfur bacteria; or treatment of the bioreactor walls to promote cell adhesion in the case of mammalian cells.

The present invention is not limited to the embodiments described and exemplified above, but is capable of variation and modification without departure from the scope of the appended claims.

We claim:

1. A disposable bioreactor for culturing microorganisms or cells, comprising flexible or semi-flexible waterproof sheets sealed along their edges to form a container, the container having a wedge shaped or rounded bottom, at the lowermost extremity of which is positioned a gas bubbler for generating gas bubbles for mixing and providing gases to microbial or cellular liquid cultures within the container, the container further comprising at least one inlet port for introducing gases or liquids and at least one exit port for exhausting gases or removing liquids wherein the exit port further comprises a coiled exhaust tube extending therefrom.

2. The disposable bioreactor of claim 1, wherein the container is generally square to rectangular except for the bottom, with a length to width ratio of about 1:1 to about 10:1.

3. The disposable bioreactor of claim 2, wherein the length to width ratio of the container is between about 2:1 and 5:1.

4. The disposable bioreactor of claim 1, wherein the container is two-sided.

5. The disposable bioreactor of claim 1, wherein the container is at least three-sided.

6. The disposable bioreactor of claim 1, wherein the container further comprises a partition extending longitudinally from the center of the container in either direction partially to the top and bottom, such that liquid in the container can flow over or under the partition.

7. The disposable bioreactor of claim 6, wherein the gas bubbler is positioned asymmetrically to one side of the partition.

8. The disposable bioreactor of claim 1, wherein the gas bubbler comprises a gas inlet port through which gas is pumped.

9. The disposable bioreactor of claim 8, wherein the gas inlet port is connected by a gas inlet tube to a gas pump.

10. The disposable bioreactor of claim 9, wherein the gas inlet tube comprises at least one filter for filtering microbial contaminants.

11. The disposable bioreactor of claim 8, wherein the gas inlet port is located at the lowermost extremity of the container.

12. The disposable bioreactor of claim 8, wherein the gas inlet port is located at the top or on a side of the container, and further comprises a tube internal to the container, which extends and is affixed to or near the lowermost extremity of the container.

13. The disposable bioreactor of claim 1, wherein the gas bubbler further comprises a gas diffuser for breaking large gas bubbles into smaller gas bubbles.

14. The disposable bioreactor of claim 1, wherein the exhaust tube is between about 3 inches and about 5 feet in length.

15. The disposable bioreactor of claim 1, wherein the exhaust tube further comprises a valve to prevent back flushing of liquids to the interior of the container.

16. The disposable bioreactor of claim 1, wherein the exhaust tube further comprises a filter for filtering microbial contaminants.

17. The disposable bioreactor of claim 1, which further comprises an inoculation port for introducing inoculafit into the container.

18. The disposable bioreactor of claim 17, wherein the inoculation port comprises a septum.

19. The disposable bioreactor of claim 1, which further comprises a breakable pouch on an interior face of the container.

20. The disposable bioreactor of claim 1, which further comprises an external reservoir in fluid communication with the container interior.

21. A kit for culturing a microorganism, which comprises:
    a) a disposable bioreactor comprising flexible or semi-flexible waterproof sheets sealed along their edges to form a container, the container having a wedge shaped or rounded bottom at the lowermost extremity of which is positioned a gas bubbler for generating gas bubbles for mixing and providing gases to microbial or cellular liquid cultures within the container, the container further comprising at least one inlet port for introducing gases or liquids and at least one exit port for exhausting gases or removing liquids wherein the exit port further comprises a coiled exhaust tube extending therefrom, and
    b) instructions for using the disposable bioreactor to culture the microorganisms.

22. The kit of claim 21, which further comprises one or more of:
    c) ingredients for preparing, or prepared culture medium for culturing the microorganism;
    d) inoculum of the microorganism to be cultured;
    e) accessories for attaching the bioreactor container to a local source of water for filling the container.
    f) accessories for connecting the bioreactor inlet port to a gas pump; and
    g) a gas pump.

23. The kit of claim 21 wherein the microbial or cellular liquid cultures consist of bacteria, cyanobacteria, fungi, algae, protozoans and nematodes.

24. A disposable bioreactor for culturing microorganisms or cells, comprising flexible or semi-flexible waterproof sheets sealed along their edges to form a container, the container having a generally square or rectangular shape, and further comprising a plurality of gas bubblers positioned across an interior floor of the container, for generating gas bubbles for mixing and providing gases to microbial or cellular liquid cultures within the container, the container further comprising at least one inlet port for introducing gases or liquids and at least one exit port for exhausting gases or removing liquids.

25. The disposable bioreactor of claim 24, wherein the length to width ratio of the container is about 1:1 to about 10:1.

26. The disposable bioreactor of claim 25, wherein the length to width ratio of the container is between about 2:1 and 5:1.

27. The disposable bioreactor of claim 24, wherein the container is two-sided.

28. The disposable bioreactor of claim 24, wherein the container is at least three-sided.

29. The disposable bioreactor of claim 24, wherein the gas bubbler comprises a gas reservoir comprising inlet holes for admitting gas bubbles from the reservoir to the container interior, the gas reservoir being operably connected to a gas inlet port through which gas is pumped.

30. The disposable bioreactor of claim 29, wherein the gas inlet port is connected by a gas inlet tube to a gas pump.

31. The disposable bioreactor of claim 30, wherein the gas inlet tube comprises at least one filter for filtering microbial contaminants.

32. The disposable bioreactor of claim 24, wherein the exit port further comprises an exhaust tube extending therefrom.

33. The disposable bioreactor of claim 32, wherein the exhaust tube is coiled.

34. The disposable bioreactor of claim 32, wherein the exhaust tube further comprises a valve to prevent back flushing of liquids to the interior of the container.

35. The disposable bioreactor of claim 32, wherein the exhaust tube further comprises a filter for filtering microbial contaminants.

36. The disposable bioreactor of claim 24, which further comprises an inoculation port for introducing inoculant into the container.

37. The disposable bioreactor of claim 36, wherein the inoculation port comprises a septum.

38. The disposable bioreactor of claim 24, which further comprises a breakable pouch on an interior face of the container.

39. The disposable bioreactor of claim 24, which further comprises an external reservoir in fluid communication with the container interior.

40. A kit for culturing a microorganism, which comprises:

a) a disposable bioreactor for culturing microorganisms or cells, comprising flexible or semi-flexible waterproof sheets sealed along their edges to form a container, the container having a generally square or rectangular shape, and further comprising a plurality of gas bubblers positioned across an interior floor of the container, for generating gas bubbles for mixing and providing gases to microbial or cellular liquid cultures within the container, the container further comprising at least one inlet port for introducing gases or liquids and at least one exit port for exhausting gases or removing liquids; and b) instructions for using the disposable bioreactor to culture the microorganism.

41. The kit of claim 40, which further comprises one or more of:

c) ingredients for preparing, or prepared culture medium for culturing the microorganism;

d) inoculum of the microorganism to be cultured;

e) accessories for attaching the bioreactor container to a local source of water for filling the container;

f) accessories for connecting the bioreactor inlet port to a gas pump; and g) a gas pump.

\* \* \* \* \*

UNITED STATES PATENT AND TRADEMARK OFFICE
CERTIFICATE OF CORRECTION

PATENT NO. : 6,432,698 B1
DATED : August 13, 2002
INVENTOR(S) : Gaugler et al.

It is certified that error appears in the above-identified patent and that said Letters Patent is hereby corrected as shown below:

Column 1,
Line 44, please delete "10" before the term "nematodes".

Column 12,
Line 8, please delete "inoculafit" and insert -- inoculant --.

Signed and Sealed this

Eighteenth Day of November, 2003

JAMES E. ROGAN
*Director of the United States Patent and Trademark Office*